(12) United States Patent
Gornushkin et al.

(10) Patent No.: US 6,987,564 B2
(45) Date of Patent: Jan. 17, 2006

(54) AUTOMATIC CORRECTION FOR CONTINUUM BACKGROUND IN LASER INDUCED BREAKDOWN AND RAMAN SPECTROSCOPY

(75) Inventors: Igor B. Gornushkin, Gainesville, FL (US); James D. Winefordner, Gainesville, FL (US); Ben W. Smith, Gainesville, FL (US)

(73) Assignee: University of Florida, Gainesville, FL (US)

( * ) Notice: Subject to any disclaimer, the term of this patent is extended or adjusted under 35 U.S.C. 154(b) by 115 days.

(21) Appl. No.: 10/411,193

(22) Filed: Apr. 11, 2003

(65) Prior Publication Data

US 2003/0231306 A1 Dec. 18, 2003

Related U.S. Application Data

(60) Provisional application No. 60/371,397, filed on Apr. 11, 2002.

(51) Int. Cl.
*G01J 3/44* (2006.01)

(52) U.S. Cl. ........................................ 356/301; 356/318
(58) Field of Classification Search ................ 356/318, 356/317, 301; 250/458.1; 702/19
See application file for complete search history.

(56) References Cited

OTHER PUBLICATIONS

P.W.J.M. Bourmans (Ed.), Inductively Coupled Plasma Emission Spectroscopy, Part 1: Methodology, Instrumentation and Performance, Wiley, New York, 1987.
A. Montaser, D.W. Golightly (Eds.), Inductively Coupled Plasmas in Analytical Atomic Spectrometry, VCH, New York, 1992.

J.B. Dawson, R.D. Shook, W.J. Proce, Background and background correction in analytical atomic spectrometry. Part 1, emission spectrometry, a tutorial review, J.Anal. At.Spectrom., vol. 8 (Jun 1993), 517-537.
E.H. van Veen, et al., Application of mathematical procedures to background correction and multivariate analysis in inductively coupled plasma—optical emission spectrometry, Spectrochim. Acta Part B 53 (1998), 639-669.
M.L. Salit, J.B. collins, D.A. Yates, Heuristic and statistical algorithms for automated emission spectral background intensity estimation, Appl. Spectrosc. 48 (1990), 109-111.

(Continued)

*Primary Examiner*—Layla G. Lauchman
(74) *Attorney, Agent, or Firm*—Miles & Stockbridge P.C.; Dennis P. Clarke

(57) ABSTRACT

The approximation of a spectral continuum by determining a plurality of minima in the spectral data; splitting the spectral data into a predetermined number of groups N; for each group of spectral data, determining major minima for the group, and calculating an average and a standard deviation for the determined major minima; determining a polynomial function that can be drawn through the major minima of all groups; for each group of spectral data, determining minor minima; calculating an average deviation ($\Phi_N$) between this polynomial function and the determined minor minima; reducing the number of groups, and repeating this process for the reduced number of groups until a minimum number of groups is reached. Then, the least $\Phi_N$ corresponding to an optimal number of groups $N_{opt}$ is determined. The spectral data is split into $N_{opt}$ groups; and a polynomial function that can be drawn through both the major minima and minor minima is determined for $N_{opt}$ groups. This polynomial function approximates the spectral continuum.

26 Claims, 15 Drawing Sheets

OTHER PUBLICATIONS

P. Taylor, P. Schutyser, Description of a computer program for quantitative spectral analysis of ICP-AES spectra generated with a high resolution computer-controlled monochromator, Spectrochim. Acta, Part B 41 (1986) 81-103.

F.Janssens, J.-P. François, An optimized background correction algorithm in automated spectral analysis based on convolution signals, Appl. Spectrosc., vol. 46, No. 2 (1992), 283-292.

B. Walczak, B. van der Bagacrt, D.L. Massart, Application of wavelet packet transform in pattern recognition of near-IR data, Anal. Chem., vol. 68, No. 10 (May 15, 1996), 1742-1747.

C.R. Mittermayr, H.W. Tan, S.D. Brown, Robust calibration with respect to background variation, Appl. Spectrosc., vol. 55, No. 7, (2001) 827-833.

J. Yang, Z. Piao, X. Zeng, Improvement of selectivity with numerical derivative techniques in inductively coupled plasma atomic emission spectrometry, Spectrochim. Acta, Part B 46, No. 6/7 (1991), 953-965.

E.H van Veen, S. Bosch, M.T.C. de Loss-Vollebregt, Quantitative line selection with Kalman filter approach for inductively coupled plasma atomic emission spectrometry, Spectrochim. Acta, Part B 48, No. 14 (1993), 1691-1701.

E.H. van Veen, S. Bosch, M.T.C. de Loss-Vollebregt, The Kalman filter approach to inductively coupled plasma atomic emission spectrometry, Spectrochim. Acta, Part B 49, No. 8 (1994), 829-846.

D. Wienke, G. Kateman, Multiresponse calibration with canonical variates in atomic emission spectroscopy of powders, Fresenius J. Anal. Chem. 343 (1992) 797-808.

R.P. Paradkar, R.R. Williams, Correcting fluctuating baselines and spectral overlap with genetic regression, Appl. Spectrosc., vol. 51, No. 1 (1997), 92-100.

I. Schechter, Correction for nonlinear fluctuating background in monovariable analytical systems, Anal. Chem. 67, No. 15, (1995) 2580-2585.

L. Xu, V. Bulatov, V. Gridin, I. Schechter, Absolute analysis of particulate materials by laser-induced breakdown spectroscopy, Anal. Chem., vol. 69, No. 11 (1997), 2103-2108.

I.B. Gornushkin, et al., Some considerations on the correlation between signal and background in laser-induced breakdown spectroscopy using single-shot analysis, Anal. Chem., vol. 71, No. 23 (Dec. 1, 1999), 5447-5449.

I.B. Gornushkin, et al., Modeling an inhomogeneous optically thick laser induced plasma: a simplified theoretical approach, Spectrochim, Acta, Part B 56 (2001) 1769-1785.

I.B. Gornushkin, et al., Identification of solid materials by correlation analysis using a microscopic laser-induced plasma spectrometer, Anal. Chem., Vo. 71, No. 22 (Nov. 15, 1999) 5157-5164.

S.I. Gornushkin, et al., An effective normalization technique for correction of matrix effects in laser induced breakdown spectroscopy detection of magnesium in powdered samples, Appl. Spectrosc., vol. 56, No. 4, 2002, 433-436.

J.M. Anzano. I.B. Gornushkin, B.W. Smith, J.D. Winefordner, Laser-induced plasma spectroscopy for plastic identification, Polymer Engineering and Science, vol. 40 (Nov. 2000), 2423-2429.

C. Chaléard, P. Mauchien, N. Andre, J. Uebbing, J.L. Lacour, C.J. Geertsen, Correction of matrix effects in quantitative elemental analysis with laser ablation optical emission spectrometry, J. Anal. At. Spectrosc., vol. 12 (Feb. 1997), 183-188.

U. Panne, C. Haisch, M. Clara, R. Niessner, Analysis of glass and glass melts during the verification of fly and bottom ashes by laser-induced plasma spectroscopy. Part II. Process analysis, Spectrochim. Acta, Part B 53 (1998) 1969-1981.

J.B. Ko, W. Sdorra, K. Niemax, On the internal standardization in optical emission spectrometry of microplasmas produced by laser ablation of solid samples, Fresenius J. Anal. Chem. 335 (1989) 648-651.

D.I. Ostrovskii, A.M. Yaremko, I.P. Vorona, Nature of background scattering in Raman spectra of materials containing high-wavenumber vibrations, J. Raman Spec. 28 (1977) 771-778.

T.J. Vickers, R.E. Wambles, Jr., C.K. Mann, Curve fitting and linearity: data processing in Raman spectroscopy, Appl. Spectrosc. vol. 55 (Nov. 4, 2001) 389-393.

V. Allen, J.H. Kalivas, R.G. Rodriguez, Post-consumer plastic identification using Raman spectroscopy, Appl. Spectrosc., vol. 53 (Nov. 6, 1999) 672-681.

302

AUTOMATIC CORRECTION FOR CONTINUUM BACKGROUND IN LASER INDUCED BREAKDOWN AND RAMAN SPECTROSCOPY

CROSS-REFERENCE TO RELATED APPLICATIONS

This study was supported by the U.S. Department of Energy Contract No. DEFG02-99-ER 14960. This application claims priority to U.S. Provisional Appl. No. 60/371,397 filed Apr. 11, 2002.

FIELD OF THE INVENTION

The invention relates to a method for the separation of material-specific portion of spectral information from the continuum background. More specifically, the inventive method approximates and eliminates the continuum background obtained in laser-induced breakdown spectroscopy (LIBS) and Raman spectroscopy using non-gated detectors.

BACKGROUND OF THE INVENTION

All experimental data contains insignificant information as well as useful information. The useful information is that from which the researcher learns an aspect of a studied object, such as a structure or composition. The insignificant information is that which the researcher wishes to unobtrusively discard without damaging essential information.

In particular, in the field of spectroscopy, the continuum contains background noise. As is known to those skilled in the art, numerical algorithms directed to background correction in spectroscopy have been developed. These methods include digital filtering, numerical derivatives, Fourier transforms, neural networks, genetic regression, wavelet transforms, principal component analysis (PCA), partial least squares (PLS), etc. These and other spectral background correction techniques are directed to the separation of an essential, material-specific portion of spectral information from its interfering part—the continuum background.

However, these known spectral background correction techniques are not adequate for all types of spectroscopy. In particular, some known background correction techniques are not robust with respect to spectrum shape and make poor background estimates when interfering lines are introduced into the spectral window. Other techniques do not compensate for the fluctuating background noise. Other techniques require prior knowledge of the analyte line position and spectrometer instrumental functions. Importantly, most known techniques require a reference spectra of pure elements to determine the positions of spectral lines and the underlying background.

The problem of background correction is particularly important in Laser Induced Breakdown Spectroscopy (LIBS) as spectra obtained in LIBS have poor reproducibility and, if a detector is not gated, high continuum background. The background can strongly vary from spectrum to spectrum and from sample to sample. Even for ablation from an ideal surface, small fluctuations in laser intensity can cause significant change in appearance of LIBS spectra. This effect is greatly multiplied for rough surfaces, surfaces that are not compositionally homogeneous, or for powders and aerosols. Adequate modeling of the background in LIBS is very important in order to improve its potential for both quantitative and qualitative analysis. Known methods of background correction do not adequately provide satisfactory background correction in LIBS.

Another technique that is frequently complicated by continuum backgrounds is Raman spectroscopy. Raman spectra contain a wealth of chemical and structural information about analyte systems, however, this information can be masked by background which overshadows inherently weak Raman signals.

The present invention overcomes the limitations of known background correction techniques in spectroscopy. In particular, the present invention is directed to approximation and automatic subtraction of continuum backgrounds obtained with non-gated detector systems in LIBS and Raman spectroscopy.

SUMMARY OF THE INVENTION

The present invention is intended to approximate a spectral continuum by determining a plurality of minima in the spectral data; splitting the spectral data into a predetermined number of groups N; for each group of spectral data, determining major minima for the group, and calculating an average and a standard deviation for the determined major minima; determining a polynomial function that can be drawn through the major minima of all groups; for each group of spectral data, determining minor minima; calculating an average deviation ($\Phi_N$) between this polynomial function and the determined minor minima; reducing the number of groups, and repeating this process for the reduced number of groups until a minimum number of groups is reached. Then, the least $\Phi_N$ corresponding to an optimal number of groups $N_{opt}$ is determined. The spectral data is split into $N_{opt}$ groups; and a polynomial function that can be drawn through both the major minima and minor minima is determined for $N_{opt}$ groups. This polynomial function approximates the spectral continuum.

DETAILED DESCRIPTION

Reference will now be made in detail to the preferred embodiments of the present invention, examples of which are illustrated in the accompanying drawings. It is to be understood that the figures and the description of the present invention included herein illustrate and describe elements that are of particular relevance to the present invention, while eliminating, for purposes of clarity, other elements will be common knowledge to one skilled in the art of spectroscopy.

It is worthy to note that any reference in the specification to "one embodiment" or "an embodiment" means that a particular feature, structure or characteristic described in connection with the embodiment is included in at least one embodiment of the invention. The appearances of the phrase "in one embodiment" in various places in the specification are not necessarily all referring to the same embodiment.

The present invention provides for finding and eliminating the plasma radiation continuum in spectroscopy, and in particular Laser Induced Plasma (LIP) and Raman Spectroscopy using non-gated detectors.

Laser Induced Plasma Spectroscopy and Raman Spectroscopy

Laser Induced Plasma (LIP) spectroscopy is very dynamic. The plasma starts from high temperatures (>20000K) and small size. During the first few tens of nanoseconds, a structureless continuum spectrum is emitted. As time progresses, the plasma expands and spectral lines appear. At first, the lines based on the pedestal of continuum emission are broad and Stark-shifted. Later, the lines become narrower and line shifts disappear. By that time (approximately 1 $\mu$s), the continuum emission offset decreases almost to the baseline (detector's dark current), which is the most favorable time to start spectra acquisition with a gated detector.

Figure 1A:
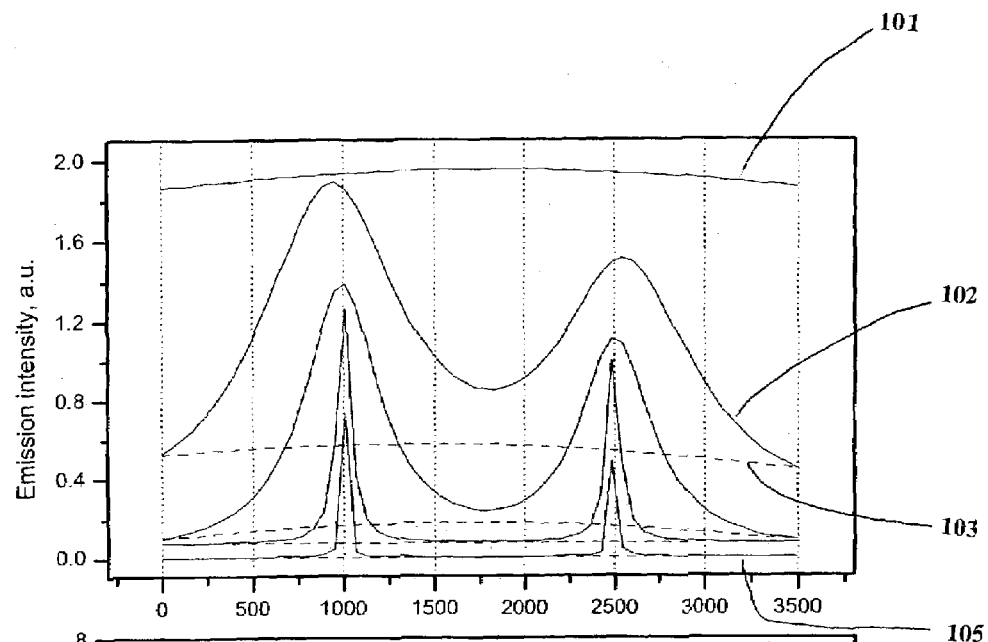
FIG. 1A illustrates an example of Laser-induced Plasma (LIP) spectrum measured by a gated detector.

FIG. 1A illustrates LIBS spectral data acquisition with a gated detector. In this example, the assumed gate width is a few tens of nanoseconds and the assumed delay times vary from zero to several microseconds. Trace 101 in FIG. 1A represents pure continuum from early plasma (zero time delay). This is the "true" baseline. Other traces in FIG. 1A correspond to later delay times and show structured emission (for example, 102) on the pedestal of continuum background (for example, 103).

Figure 1B:
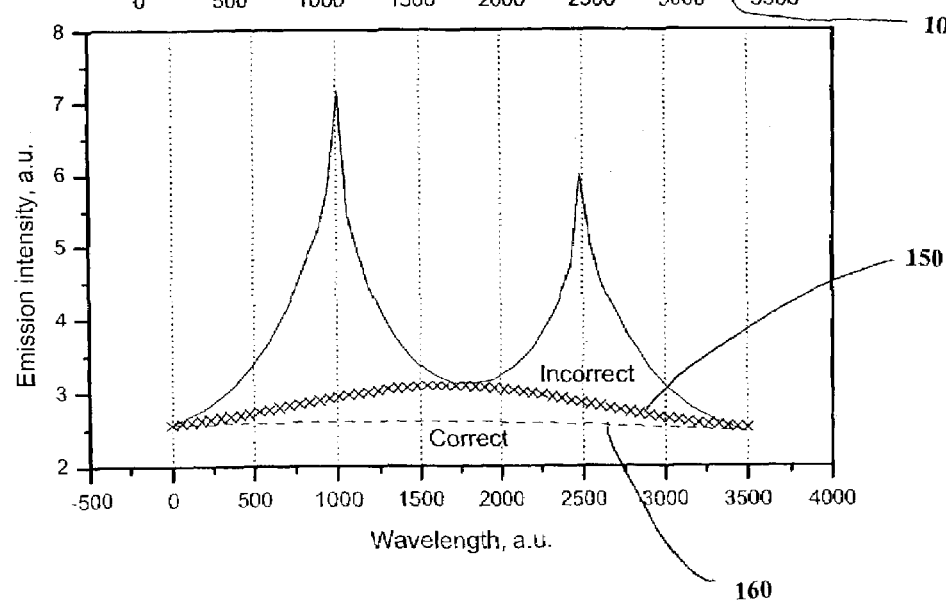
FIG. 1B illustrates an example of LIP spectrum measured by a non-gated detector.

With a non-gated detector, however, these events are not time-resolved and the resulting spectrum is a complex superposition of plasma emissions at all times. FIG. 1B illustrates LIBS spectral data acquisition with a non-gated detector. The multiple traces shown in FIG. 1A are representative of spectrum snapshots at different times, whereas the trace in FIG. 1B illustrates a time-integrated spectrum obtained by the summation of all traces in FIG. 1A.

As can be seen, there are many differences between the gated and non-gated detection modes. For example, if LIBS spectrum 105 in FIG. 1A (and the corresponding delay time with respect to the plasma initiation) is chosen as a starting point for the data collection with a gated detector, then further processing of spectral information is straightforward because the positions of the lines and the baseline are well determined. With the non-gated detector in FIG. 1B, however, the situation is more complex. The lines are asymmetric and unresolved due to their early shifts and breadths. Furthermore, the continuum background is indistinguishably merged into the time-integrated spectrum.

In one embodiment, the inventive method and system is directed to finding and eliminating the plasma radiation continuum in LIP spectroscopy. Plasma continuum emission is a complex mixture of free-free radiation, recombination (or free-bound) radiation, negative ion emission, and pseudo-continuum of strongly broadened lines. When correcting the background, it is desirable to retain a maximum of element-specific information. This is important for reliable material identification, for example. Therefore, in the present invention, the pseudo-continuum is not considered to be part of the background continuum, and is therefore not eliminated in the background correction process. Only free-free, free-bound, and negative ion radiation constitute the continuum background that is eliminated by the method and system of the present invention. The retained portion of the spectrum is thus purely material-specific and allows for rapid qualitative or quantitative analysis.

The algorithm of the present invention is not directed to reduction of noise, but is optimized to eliminate only continuous radiation background.

FIG. 1B illustrates two baselines. Baseline 150 includes not include the pseudo-continuum, whereas baseline 160 does includes the pseudo-continuum. Comparing FIG. 1A and FIG. 1B, it is obvious that baseline 160 is much closer to the "true" baseline—101 in FIG. 1A.

The present invention provides for correcting for the continuum background without information about the positions of spectral lines and the underlying background. Other continuum correction algorithms know to those skilled in the art typically require reference spectra of pure elements to determine these positions. In the present invention, the position of continuum background is determined for each spectrum individually, and reference spectra is not required.

In another embodiment, the present invention provides for background continuum correction in Raman spectroscopy using non-gated detectors as well as LIP. The background signals in Raman spectra often obscure Raman signals making spectral analysis, identification and quantitation difficult.

Raman spectroscopy with a non-gated detector results in broad band spectra similar to LIP spectra. In addition, Raman spectroscopic background is likewise complex and not easily modeled. In addition, non-gated detectors are prominent in Raman spectroscopy. The elimination of pseudo-continuum as a background contributing factor applies to the relatively broad bands common to Raman spectra as well as LIP spectra.

Inventive Background Correction Procedure

Figure 2:
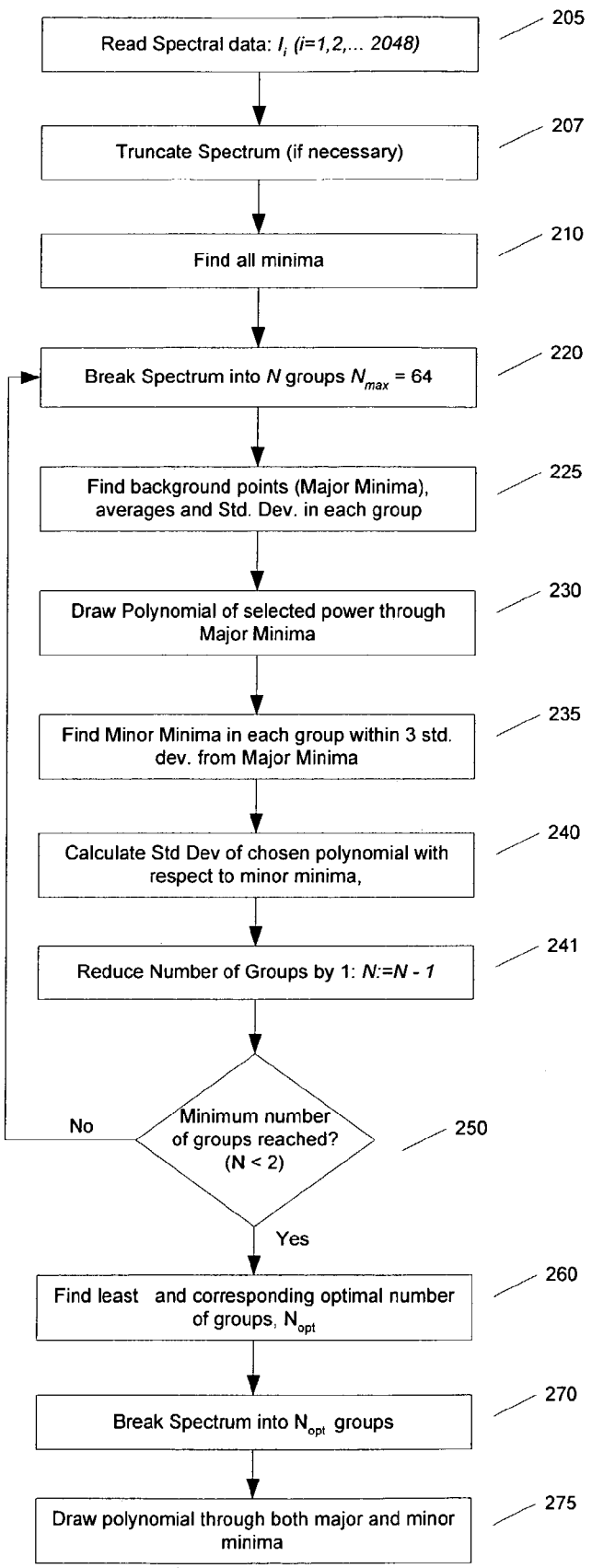
FIG. 2 is a block diagram illustrating the background correction method of the present invention.

FIG. 2 illustrates a block diagram of the background correction procedure of the present invention. In the embodiment exemplified by FIG. 2, a specific CCD detector with a 1-dimensional 2048 pixel photodiode array is used. However, the algorithm can easily be modified for detectors with arbitrary numbers of photo sensitive elements.

At step 205, spectral data from the photodiode array is read. The spectrum is truncated at step 207, if necessary. All minima on the spectrum are determined at step 210. The spectrum is split in to a certain number (N) of groups at step 220. Preferably, 64 initial groups are used, each containing 32 pixels. The maximum number of groups on any iteration is preferably 64.

At step 225, background points are selected within each group. Preferably, only $\frac{1}{16}^{th}$ (approximately 6%) of the total number of pixels in each group are allowed to be background pixels. These are the pixels with the minimal intensities, referred to as "major minima". In a preferred embodiment, the minimal number of background pixels (major minima) is two. If two major minima cannot be found within a group, the initial number of groups is automatically reduced. This may occur, for example, when a truncated (<2048 pixel) spectrum is used. Means and standard deviations are also calculated for the major minima within each group at step 225.

A polynomial function is preferably used for background approximation as polynomial functions are sufficiently general and easily computable. That is, a polynomial functions are able to approximate a large class of functions that might constitute the "true" background function, and they allow rapid calculations at any desired points where interpolation or extrapolation are required. The preferred maximum polynomial power is 10, as functions that use higher powers may experience strong oscillations.

The polynomial is drawn through major minima at step 230. In a preferred embodiment, this is accomplished using least squares fitting. As will be obvious to one skilled in the art, other methods are known, and may be used in alternative embodiments. The polynomial power may be predetermined, or alternatively, it may be automatically selected based on minimal standard deviation between the polynomial of a certain power (from 1 to 10) and the data points (background). The procedure based on the F-test can also be applied for choosing the polynomial power.

Other groups of minima, such as the minor minima, are determined for each group at step 235. Preferably, minor minima are pixels whose intensities fall within 3 standard deviations from the major minima.

The sum of squares of the deviations between the points approximated by the polynomial and all minor minima is then calculated and averaged at step 240. This quantity is denoted $\Phi_N$ and serves as a criteria for selecting the optimal number of groups for splitting the spectrum.

In the next iterations, the number of groups (N) is sequentially reduced by one at 241, and the procedure from step 220 to 241 is repeated until the minimal allowed number of groups is reached (step 250). In a preferred embodiment, the minimal number of groups is three. These iterations result in an array of $\Phi_N$ values.

Based on this array, group numbers corresponding to the smallest $\Phi_N$ values are retained at step 260 for further analysis. In a preferred embodiment, three group numbers are retained. Among the retained group numbers, the group number is selected which yields fewer data points lying under the fitting polynomial curve. This is the optimal number of groups $N_{OPT}$. Typically, it corresponds to the minimal $\Phi_N$, as an acceptable line can be drawn through only the detector dark current noise minima, providing that the polynomial correctly approximates the continuum background. The spectrum is then broken into this optimal number of groups and the polynomial is then redrawn through all minima, both major and minor, at steps 270 and 275.

FIGS. 3A–3D illustrate examples of different stages of the polynomial determined by the inventive algorithm to approximate the continuous radiation background. In the figures, dots represent minima (both major and minor).

Figure 3A:
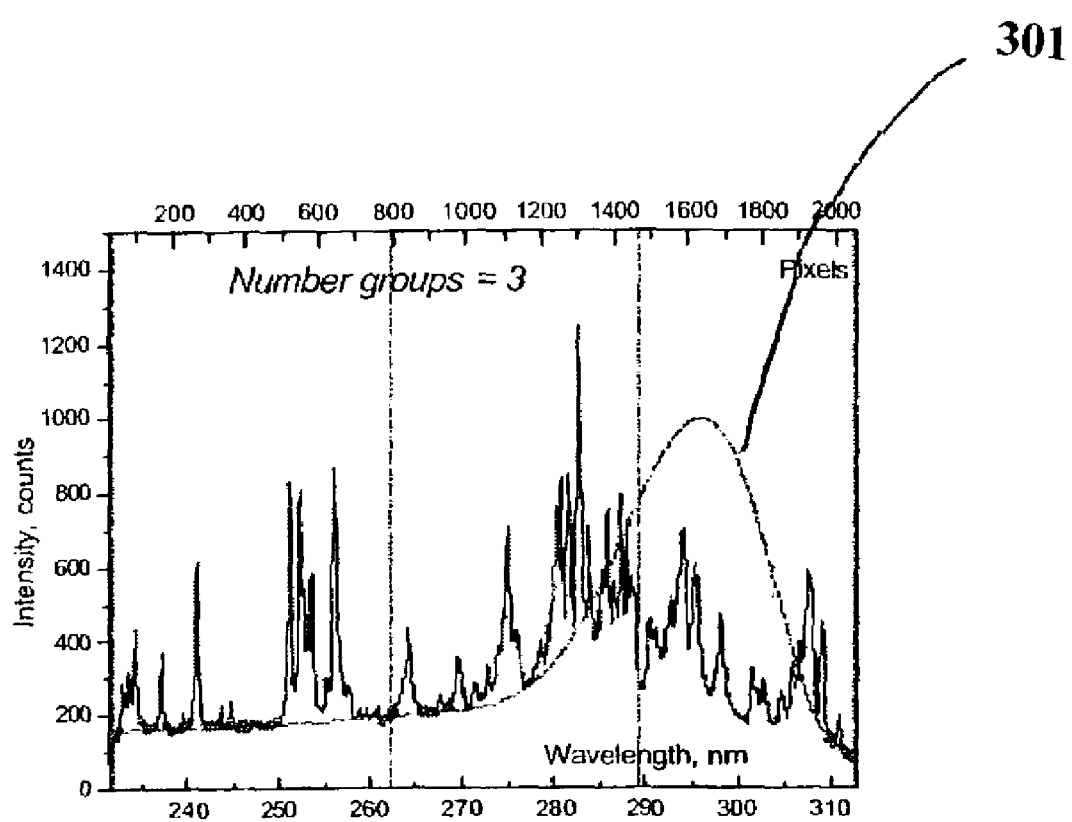
FIGS. 3A–3D illustrate stages of background approximation using the method and system of the present invention.

FIG. 3A illustrates a scenario of poor background approximation with an inadequately small number of groups. The spectrum here is divided only into three groups, and the polynomial is drawn through the chosen minima almost exactly. That is, the sum of the averaged squared deviations is minimal. As there are too many points under polynomial curve 301, this approximation is rejected.

Figure 3B:
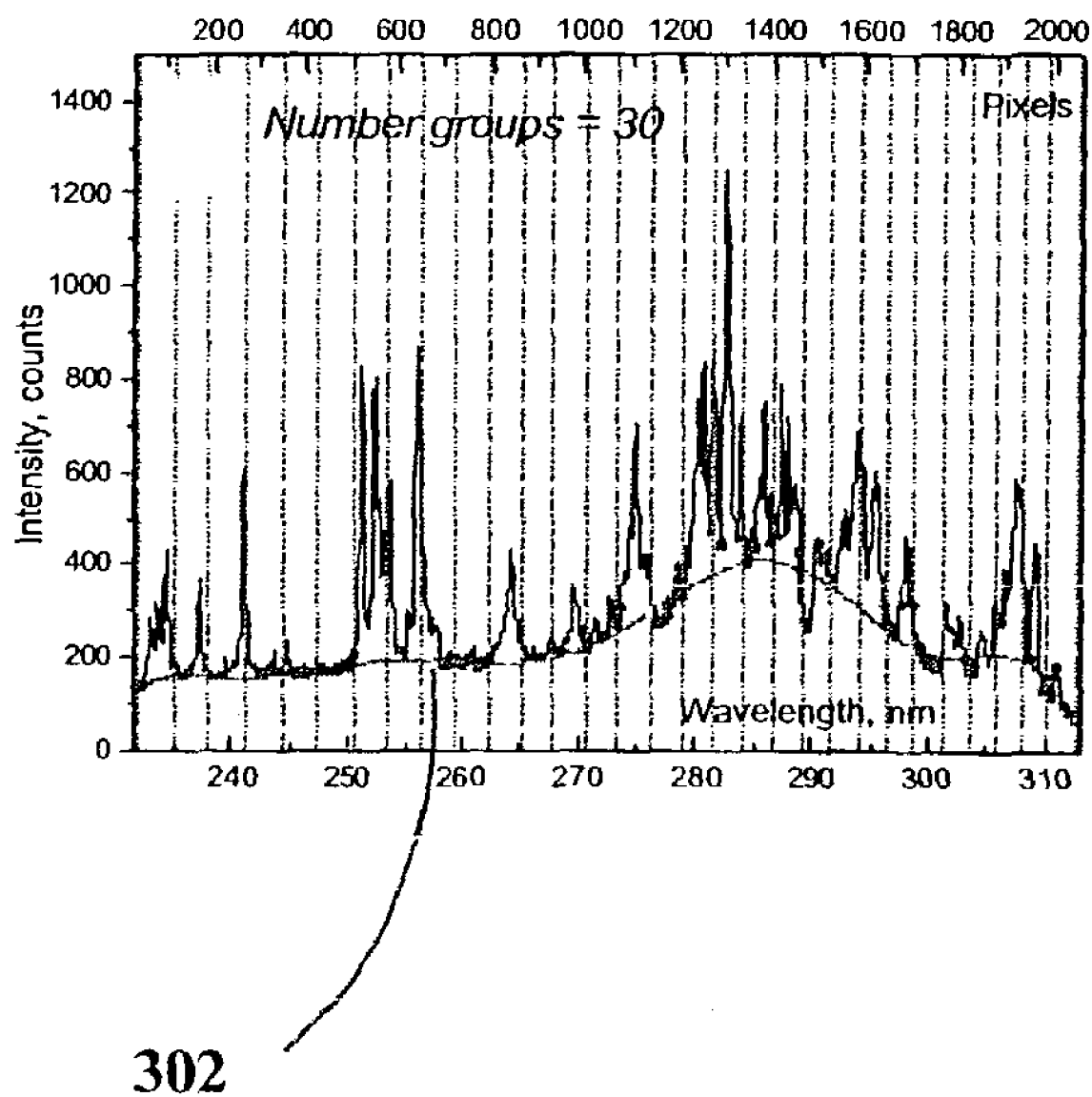

FIG. 3B illustrates the case where N=30, that is, the spectrum is divided into 30 groups. In this example, the background line is more detailed, and encompasses many spectrum bumps and falls, and is a close approximatation. However, the background is not a desirable approximation as it includes the pseudo continuum of interfering lines. In the inventive algorithm, the spectrum in FIG. 3B, i.e. N=30, is rejected on the basis of a large sum of averaged squared deviations, $\Phi_N$.

Figure 3C:
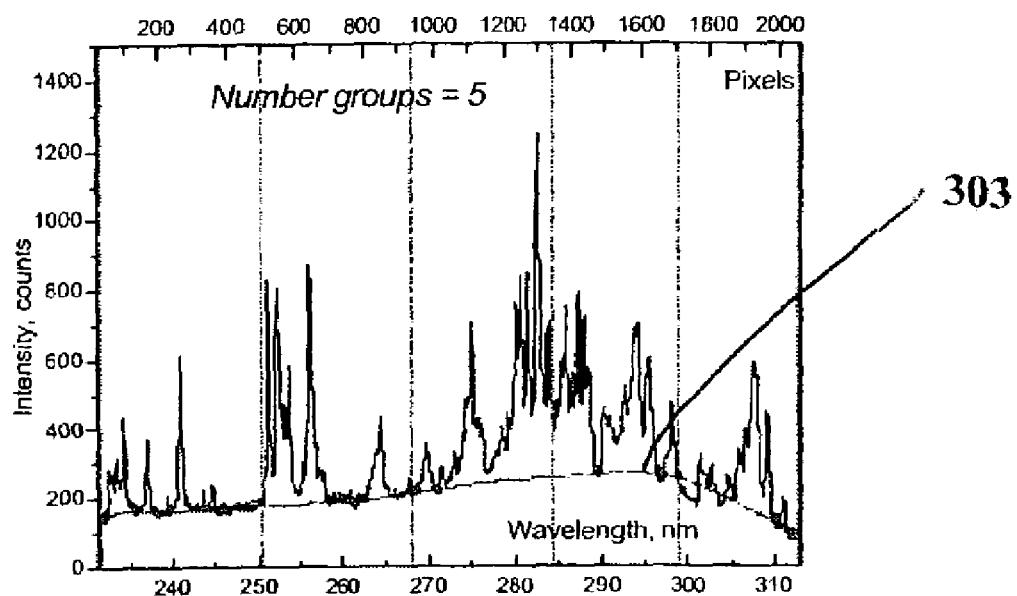

The spectrum in FIG. 3C provides minimal $\Phi_N$ of 5. However, this is not the optimal background approximation as the approximation of the right part of the spectrum is imprecise leaving too many points under the fitting curve.

Figure 3D:
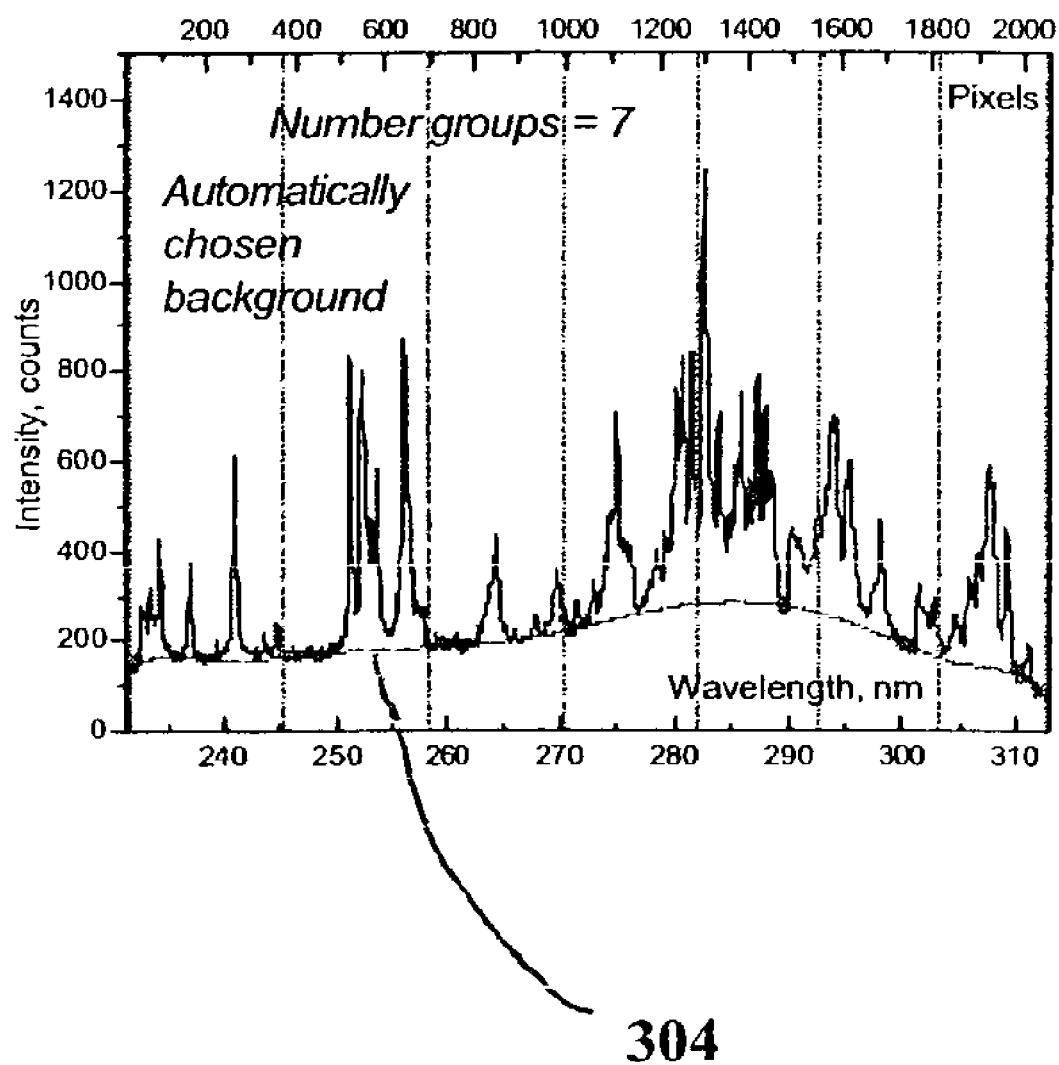

In this example, the inventive system automatically chooses the polynomial shown in FIG. 3D as the optimal approximation, with N=7. The polynomial in FIG. 3D goes through all line-free zones and under regions with strongly interfering lines. This is the best line that can be drawn to separate continuum background from structured spectrum for this example.

Figure 4:
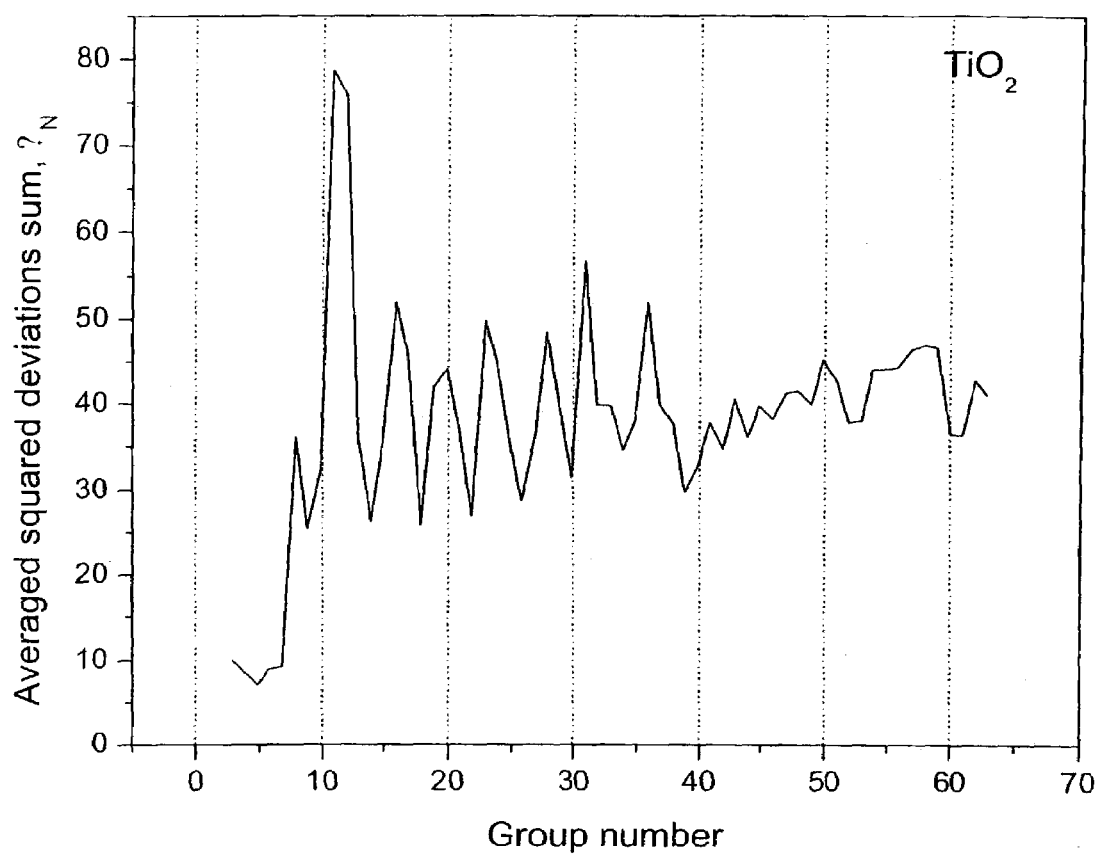
FIG. 4 illustrates sum of averaged squared deviations as a function of spectrum divisions.

FIG. 4 illustrates the dependence of the sum of averages squared deviations, $\Phi_N$, upon the number of groups. The optimal number of groups (i.e. the smallest $\Phi_N$) for the spectrum of FIG. 3 lies between 3 and 7. In this example, as illustrated by FIG. 3D, N=7 is the optimal choice for number of groups, as minimal data points are under the approximating polynomial.

Figure 5A:
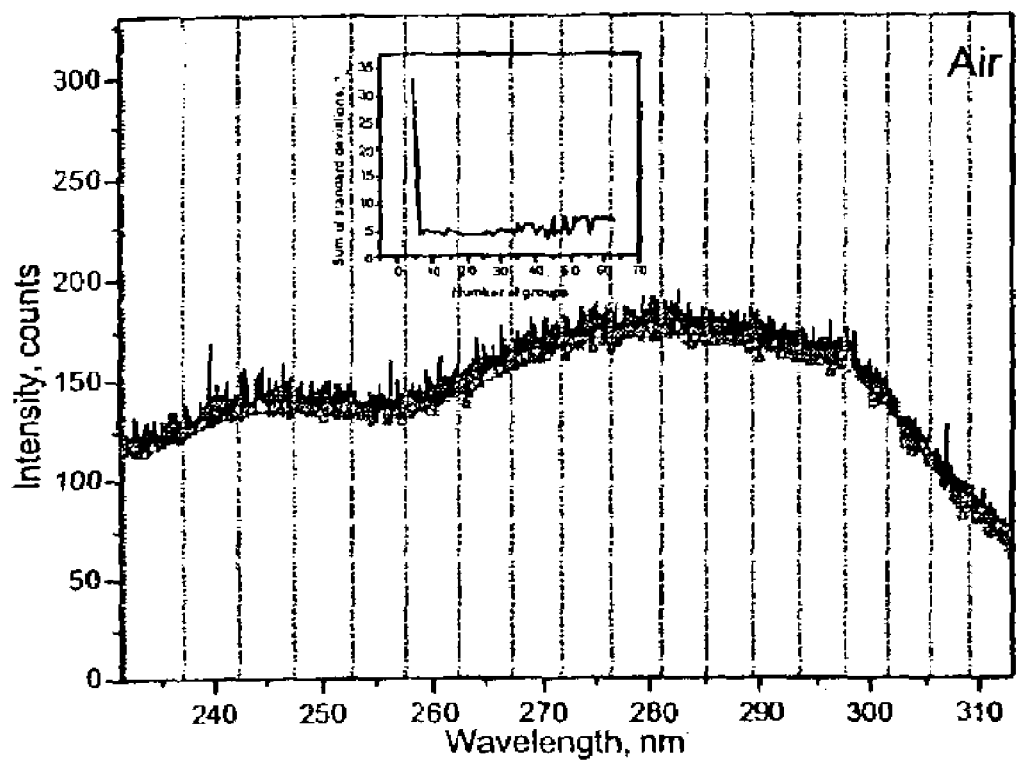
FIGS. 5A–5D illustrate examples of applying the inventive background correction algorithm to line-poor LIB spectra.
Figure 5B:
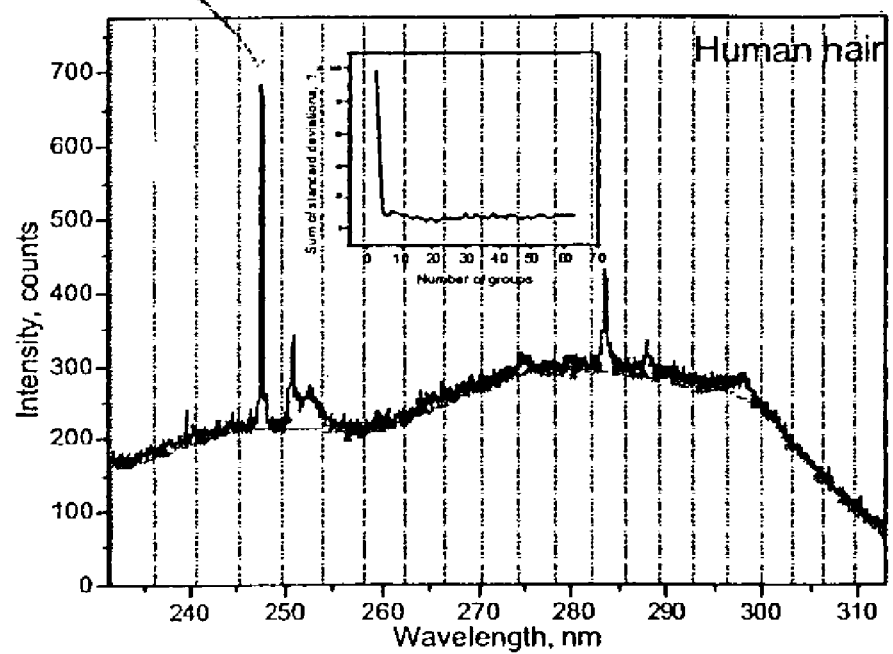
Figure 5C:
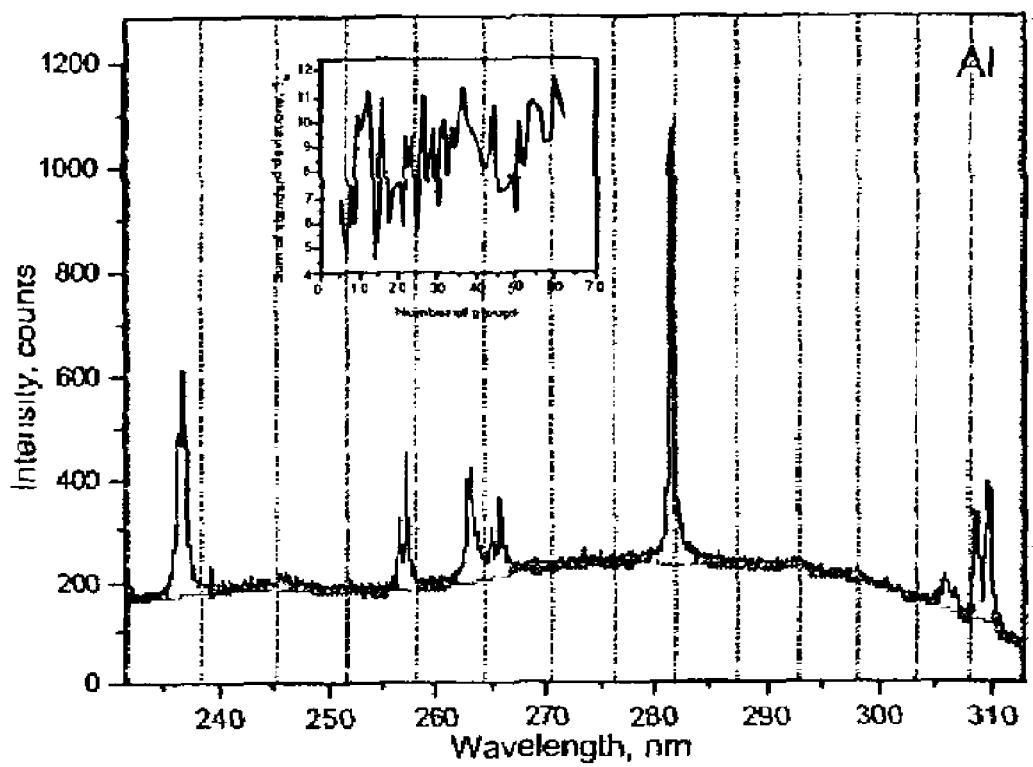
Figure 5D:
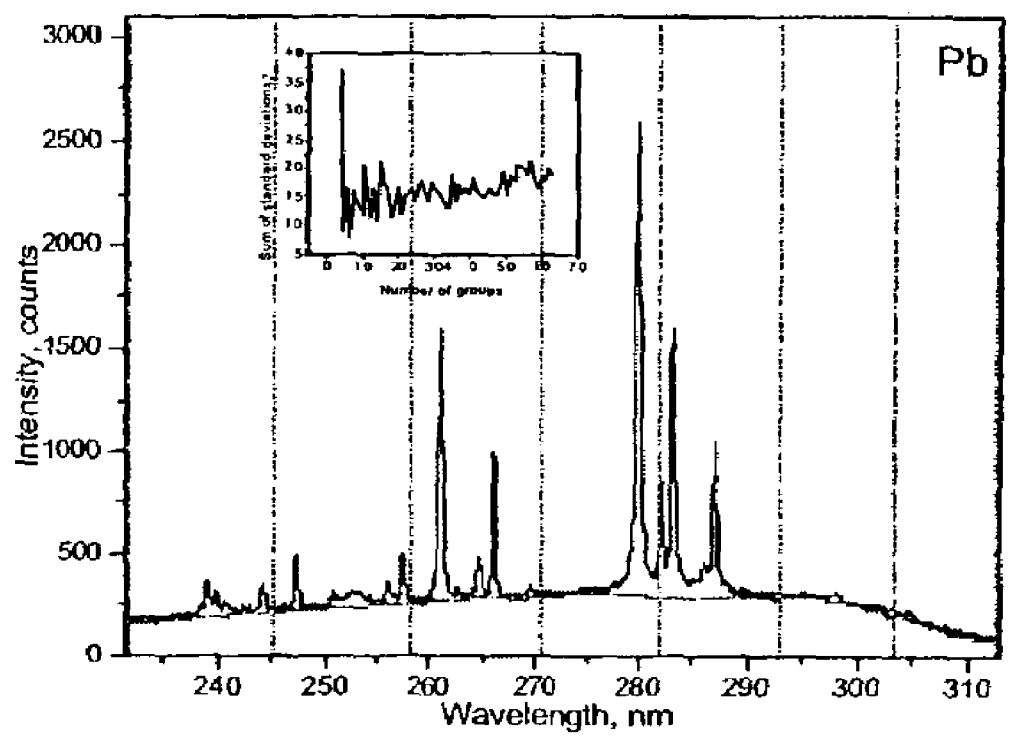
Figure 6A:
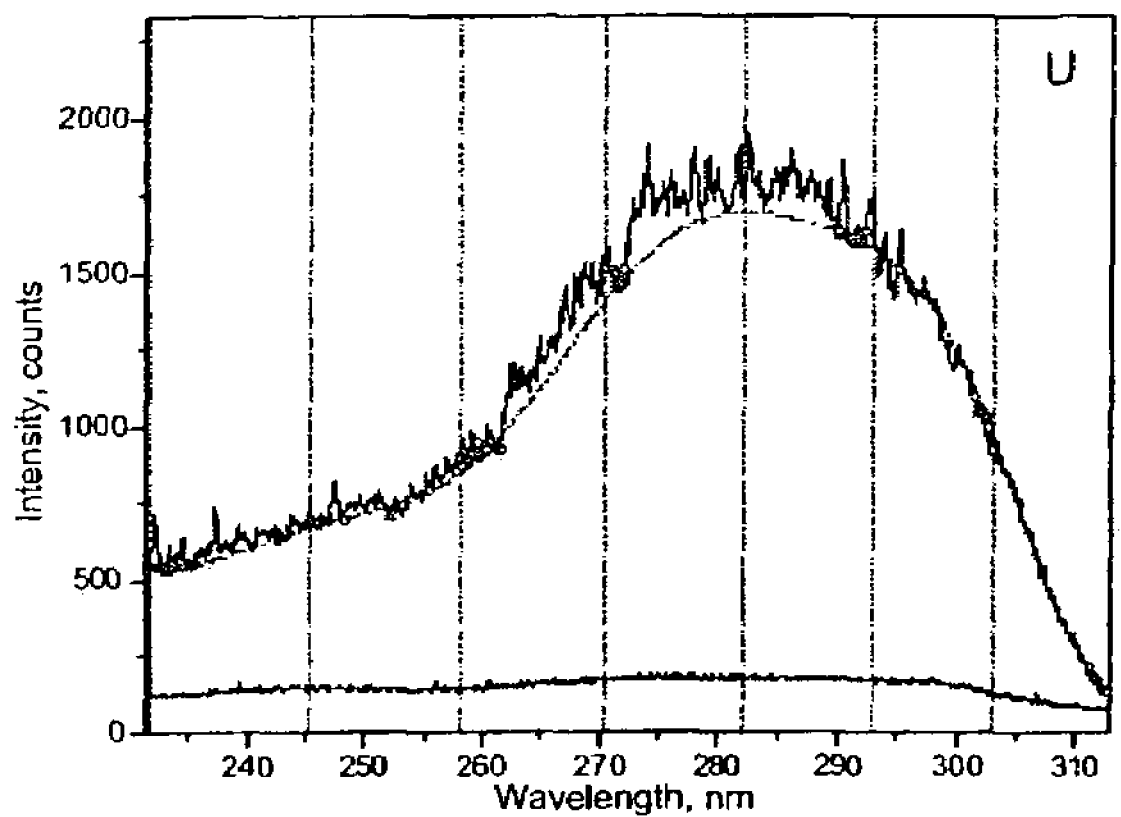
FIGS. 6A–6D illustrate examples of applying the inventive background correction algorithm to line-rich LIB spectra.
Figure 6B:
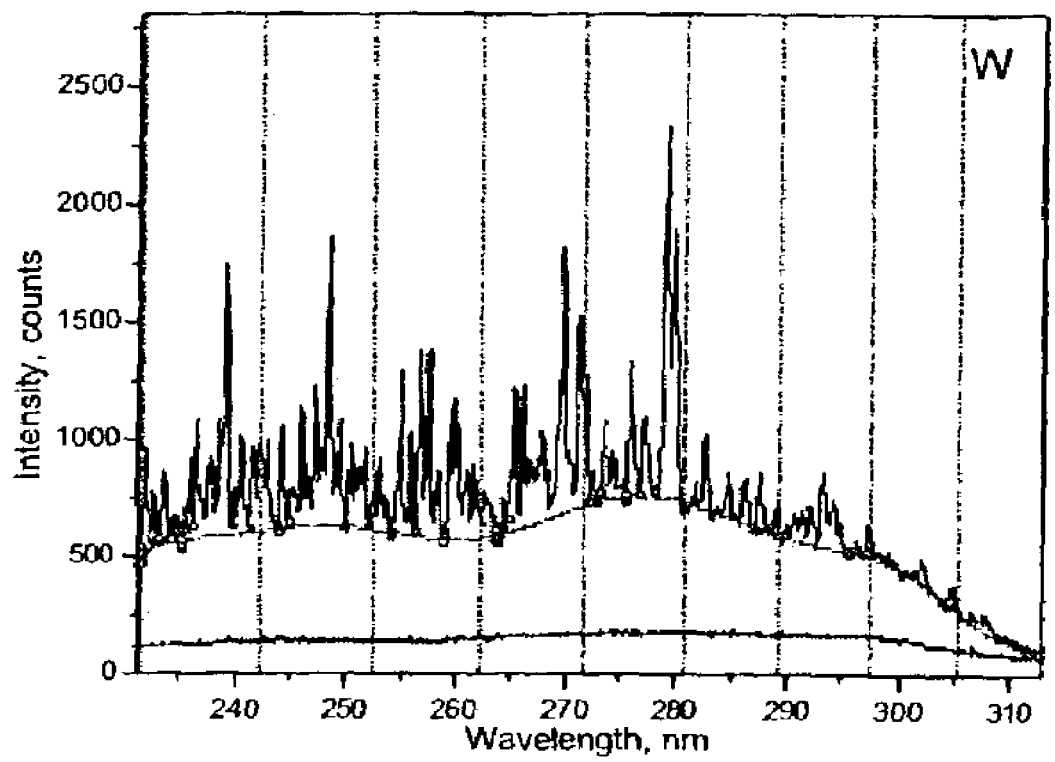
Figure 6C:
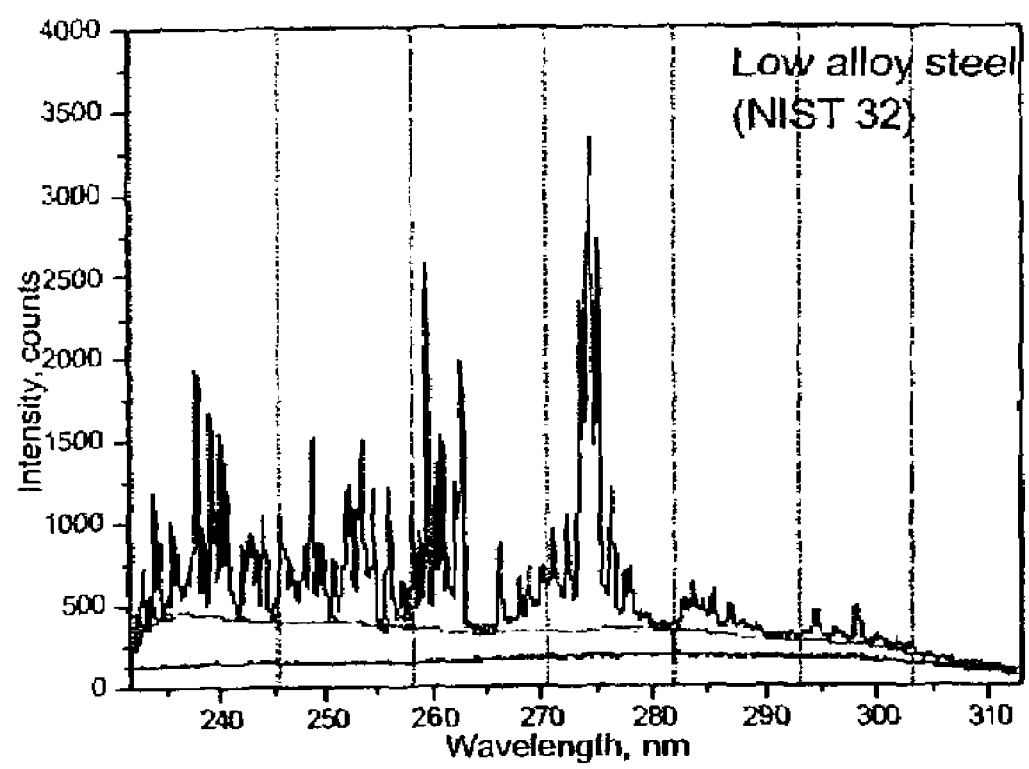
Figure 6D:
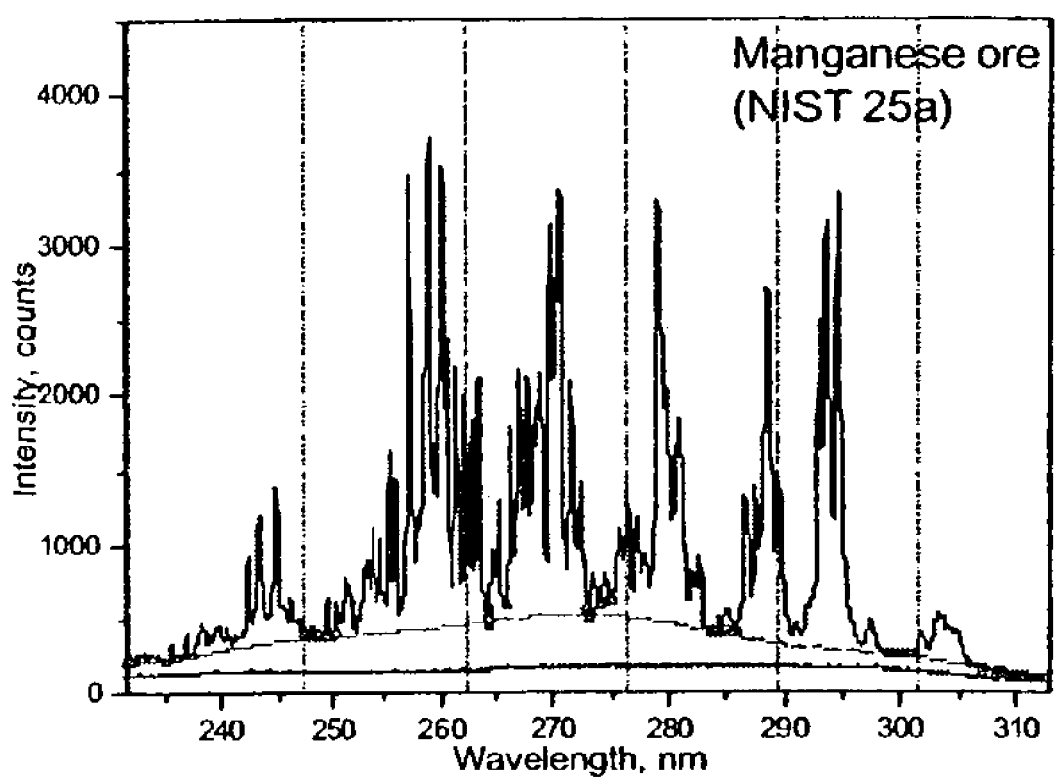

FIGS. 5A–5D illustrate examples of the background correction algorithm of the present invention applied to simple LIB spectra. The spectra in FIG. 5 is simple, or "line-poor" as it contains only a few isolated lines or a few groups of slightly interfering lines. FIG. 5A is an example of air LIB spectra, FIG. 5B is an example of human hair LIB spectra, FIG. 5C is an example of aluminum spectra and FIG. 5D is an example of lead spectra. As shown, these spectra all contain large regions free from spectral lines. In these regions, continuum background points are easily identified.

As shown in FIG. 5A, the air spectrum exhibits continuum with no lines. This continuum should be a part of any spectrum obtained from any material in air. The air-continuum contribution is significant when the plasma is air dominating, that is, the amount of target material in the plasma is small compared to the air constituents. This is often the case for organic materials. The laser spark induced on a surface of an organic target is typically weaker than that on metal. Its spectrum, at least in the UV spectral range, is line-poor and contains only a few lines.

FIG. 5B illustrates the LIB spectrum of human hair. As shown in FIG. 5B, the spectrum has the same shape as the air spectrum in FIG. 5A, and exhibits only a few spectral lines, the most prominent of which is carbon at 247 mm, as shown by peak 505. The inserts in FIGS. 5A–5D illustrate variations in $\Phi_N$ as a function of spectra divisions.

As the plasma shifts from air dominating to target dominating, the shape of background continuum can change significantly, as shown in FIGS. 5C and 5D. The air background continuum can still be seen in the aluminum spectrum in FIG. 5C, and to a smaller extent, in the lead spectrum in FIG. 5D. As shown, background spectra is strongly affected by the material. Continuum background underlying each structure spectrum should, therefore, be treated individually.

FIGS. 6A–6D illustrate complex, or "line-rich" spectra. These spectra consist of regions of strongly overlapped and/or unresolved lines. The continua due to recombination radiation and due to strong line overlap are indistinguishable. There are very few (or no) points in the spectrum that belong to the true baseline. Simple visual analysis of such a spectrum provides no information about how these points can be determined. Therefore, the background will always be overestimated in the case of a line-rich spectrum. The approximated background will necessarily include the portion of a structured spectrum that contains strongly overlapping lines. Every spectrum, however, has deep depression regions in which the algorithm finds the "background" points. The polynomial determined by the inventive method drawn through these points will deviate from the true background. However, the deviation is not very significant as the spectrum retains most of the target-specific information after subtraction.

One important application of the inventive method is in the use of LIBS spectra in material identification. In such an application, linear correlation may be used for identification using reference spectral libraries.

Another application of the inventive algorithm is to correct emission signal instability in LIBS. The precision of LIBS is typically modest, due to large emission intensity fluctuations that occur because of the strongly non-linear character of light-matter interaction. The inventive algorithm can easily extract the continuum background from any spectrum and integrate it.

As discussed above, the inventive algorithm can be applied to areas of spectroscopy other than LIBS, including Raman spectroscopy. The prominence of non-gated detectors used in Raman spectroscopy make the present invention an especially important technique in Raman spectroscopy.

In one embodiment of the present invention, the inventive algorithm is used in a piecewise approach in conjunction with single polynomial function fitting as described above. The application is particularly useful for Raman spectroscopy, as the background signals in Raman spectra obscuring Raman signals are often very complex and difficult to model.

Any method known to those skilled in the art could be used to implement the inventive algorithm as a computer program. For example, a computer program written in Visual Basic and Visual C++ may be used to implement the inventive algorithm. As will also be known to those skilled in the art, the algorithm may alternatively be implemented in hardware.

While the invention has been described in conjunction with specific embodiments thereof, it is evident that many alternatives, modifications and variations will be apparent to those skilled in the art. Accordingly, the preferred embodiments of the invention as set forth herein, are intended to be illustrative, not limiting. Various changes may be made without departing from the spirit and scope of the invention as set forth herein and defined in the claims.

What is claimed is:

1. A method of approximating a spectral continuum, comprising:
    (a) obtaining spectral data;
    (b) determining a plurality of minima in the spectral data;
    (c) splitting the spectral data into a predetermined number of groups N;
    (d) for each group of spectral data, determining major minima for the group, and calculating an average and a standard deviation for the determined major minima;
    (e) determining a polynomial function that can be drawn through the major minima of all groups as determined in step (d);
    (f) for each group of spectral data, determining minor minima;
    (g) calculating an average deviation ($\Phi_N$) between the polynomial function determined in step (e) and the minor minima determined in step (f);
    (h) reducing the number of groups, and repeating steps (c)–(g) for the reduced number of groups;
    (i) determining a least $\Phi_N$ and corresponding optimal number of groups $N_{opt}$;
    (j) splitting the spectral data into $N_{opt}$ groups; and
    (k) determining a polynomial function that can be drawn through both the major minima and minor minima determined for $N_{opt}$ groups;

wherein said polynomial function determined in step (k) approximates the spectral continuum.

2. The method of claim 1, wherein said determining major minima in step (d) comprises determining pixels in the group that are in the plurality of minima determined in step (b).

3. The method of claim 1, wherein step (a) comprises reading spectral data from a photodiode array.

4. The method of claim 3, wherein said photodiode array is a 2048 pixel photodiode array, the predetermined number of groups N is 64, and each group contains 32 pixels.

5. The method of claim 1, wherein at least 2 major minima are determined for each group in step (d).

6. The method of claim 1, wherein said polynomial function determined in step (d) has a power between 1 and 10.

7. The method of claim 1, wherein step (e) comprises using least squares fitting to determine a polynomial function.

8. The method of claim 1, wherein said determining minor minima in step (f) comprises determining pixels whose intensities fall within 3 standard deviations from the major minima determined in step (d).

9. The method of claim 1, wherein steps (c)–(g) are repeated until a minimal number of groups is reached.

10. The method of claim 1, wherein step (h) additionally comprises reducing the number of groups by 1.

11. The method of claim 1, wherein said spectral data obtained in step (a) is Raman spectroscopic data.

12. The method of claim 1, wherein said spectral data obtained in step (a) is LIP spectroscopic data.

13. The method of claim 1, wherein a non-gated detector was used to generate said spectral data.

14. A computer-readable medium containing instructions that cause a computer to approximate a spectral continuum, said medium comprising:
    a first code section containing instructions that cause the computer to obtain spectral data;
    a second code section containing instructions that cause the computer to determine a plurality of minima in the spectral data;
    a third code section containing instructions that cause the computer to split the spectral data into a predetermined number of groups N;
    a fourth code section containing instructions that cause the computer to determine major minima for each group, and calculate an average and a standard deviation for the determined major minima for each group;
    a fifth code section containing instructions that cause the computer to determine a polynomial function that can be drawn through the major minima of all groups determined by the fourth code section;
    a sixth code section containing instructions that cause the computer to determine minor minima for each group of spectral data;
    a seventh code section containing instructions that cause the computer to calculate an average deviation ($\Phi_N$) between the polynomial function determined by the fifth code section and the minor minima determined by the sixth code section;
    an eighth code section containing instructions that cause the computer to reduce the number of groups and repeat the third, fourth, fifth, sixth and seventh code sections for the reduced number of groups;
    a ninth code section containing instructions that cause the computer to determine a least $\Phi_N$ and corresponding optimal number of groups $N_{opt}$;

a tenth code section containing instructions that cause the computer to split the spectral data into $N_{opt}$ groups; and an eleventh code section containing instructions that cause the computer to determine a polynomial function that can be drawn through both the major minima and minor minima determined for $N_{opt}$ groups;

wherein said polynomial function determined by the eleventh code section approximates the spectral continuum.

15. The computer-readable medium of claim 14, wherein said fourth code section contains instructions that cause the computer to determine major minima by determining pixels in the group that are in the plurality of minima determined by the instructions in the second code section.

16. The computer-readable medium of claim 14, wherein said first code section contains instructions that cause the computer to read spectral data from a photodiode array.

17. The computer-readable medium of claim 16, wherein said photodiode array is a 2048 pixel photodiode array, the predetermined number of groups N is 64, and each group contains 32 pixels.

18. The computer-readable medium of claim 14, wherein at least 2 major minima are determined for each group by the instructions in the fourth code section.

19. The computer-readable medium of claim 14, wherein said polynomial function determined by the instructions in the fifth code section has a power between 1 and 10.

20. The computer-readable medium of claim 14, wherein said instructions in the fifth code section uses least squares fitting to determine a polynomial function.

21. The computer-readable medium of claim 14, wherein said sixth code section determines minor minima by determining pixels whose intensities fall within 3 standard deviations from the major minima determined by the instruction in the fourth code section.

22. The computer-readable medium of claim 14, wherein instructions in the third, fourth, fifth, sixth and seventh code sections are repeated until a minimal number of groups is reached.

23. The computer-readable medium of claim 14, wherein said instructions in the eight code section additionally comprise reducing the number of groups by 1.

24. The computer-readable medium of claim 14, wherein said spectral data obtained by the instructions in the first code section is Raman spectroscopic data.

25. The computer-readable medium of claim 14, wherein said spectral data obtained by the instructions in the first code section is LIP spectroscopic data.

26. The computer-readable medium of claim 14, wherein a non-gated detector was used to generate said spectral data.

* * * * *